United States Patent [19]
Petrofsky et al.

[11] Patent Number: 4,492,233
[45] Date of Patent: Jan. 8, 1985

[54] METHOD AND APPARATUS FOR PROVIDING FEEDBACK-CONTROLLED MUSCLE STIMULATION

[75] Inventors: Jerrold S. Petrofsky, Beavercreek; Roger M. Glaser, Dayton; Chandler A. Phillips, Tipp City, all of Ohio; Steven H. Petrofsky, Florissant, Mo.

[73] Assignee: Wright State University, Dayton, Ohio

[21] Appl. No.: 417,934

[22] Filed: Sep. 14, 1982

[51] Int. Cl.³ .............................................. A61N 1/36
[52] U.S. Cl. ..................................... 128/421; 128/774; 128/905
[58] Field of Search ................... 73/379; 128/421–423, 128/707, 741, 774, 782, 905

[56] References Cited

U.S. PATENT DOCUMENTS

| | | | |
|---|---|---|---|
| 1,498,529 | 6/1924 | Allen | 128/796 |
| 3,083,712 | 4/1963 | Keegan, Jr. | 128/423 W |
| 3,204,637 | 9/1965 | Frank et al. | 128/423 W |
| 3,387,147 | 6/1968 | Radwan | 307/275 |
| 3,565,080 | 2/1971 | Ide et al. | 128/422 |
| 3,628,538 | 12/1971 | Vincent et al. | 128/422 |
| 3,817,254 | 6/1974 | Maurer | 128/421 |
| 3,888,261 | 6/1975 | Maurer | 128/420 |
| 3,911,910 | 10/1975 | Oesau | 128/82.1 |
| 3,929,335 | 12/1975 | Malick | 272/57 |
| 3,983,881 | 10/1976 | Wickham | 128/421 |
| 4,023,574 | 5/1977 | Nemec | 128/420 |
| 4,071,033 | 1/1978 | Nawracaj et al. | 128/420 |
| 4,126,137 | 11/1978 | Archibald | 128/422 |
| 4,147,171 | 4/1979 | Greene et al. | 128/421 |
| 4,148,321 | 4/1979 | Wyss et al. | 128/420 |
| 4,157,087 | 6/1979 | Miller et al. | 128/741 |
| 4,165,750 | 8/1979 | Aleev et al. | 128/422 |
| 4,177,819 | 12/1979 | Kofsky et al. | 128/422 |
| 4,195,626 | 4/1980 | Schweizer | 128/774 |
| 4,236,528 | 12/1980 | Stanec et al. | 128/782 |
| 4,278,095 | 7/1981 | Lapeyre | 128/707 |
| 4,333,340 | 6/1982 | Elmeskog | 73/379 |
| 4,358,105 | 11/1982 | Sweeney, Jr. | 73/379 |
| 4,392,496 | 7/1983 | Stanton | 128/423 |

FOREIGN PATENT DOCUMENTS

| | | |
|---|---|---|
| 0033747 | 8/1981 | European Pat. Off. . |
| 2101960 | 4/1979 | Fed. Rep. of Germany ...... 128/782 |
| 2052994 | 2/1981 | United Kingdom . |
| 635995 | 12/1978 | U.S.S.R. . |
| 719635 | 3/1980 | U.S.S.R. . |

OTHER PUBLICATIONS

Article by G. Keith Stillwell entitled "Clinical Electric Stimulation", published on an unknown date in a text of unknown title (reference being made particularly to pp. 114 through 117.
Article by Peckham et al. appearing at pp. 83 through 95 in a text entitled "Functional Electrical Stimulation", Marcel Dekker, Inc., 1977.
Control of a Skeletal Joint by Electrical Stimulation of Antagnoists, Vodovnik et al., Med. & Biol. Engn., vol. 5, pp. 97–109, Pergamon Press, 1967.
"Variability of Electrically Evoked Muscle Contractions with Special Regard to Closed Loop Controlled Orthosis", Trnkoczy, Annals of Biomedical Engineering 2, 226–238, (1974).
(List continued on next page.)

Primary Examiner—William E. Kamm
Assistant Examiner—Mitchell J. Shein
Attorney, Agent, or Firm—Biebel, French & Nauman

[57] ABSTRACT

A method and apparatus for stimulating a human muscle to produce a controlled response against a dynamic load. Muscle stimulation is achieved through a pair of alternately pulsed stimulation signals which are applied across different pairs of stimulation electrodes. A pulse generating circuit generates the pulsed stimulating signals at a frequency of about 60 Hz across each electrode pair. A position sensor provides a feedback signal to a computer, which in turn generates a stimulation control signal. The pulse generating circuit uses the stimulation control signal for adjusting the amplitude of the stimulation pulses. The pulse width of the stimulation pulses is disclosed as being about 500 microseconds.

17 Claims, 8 Drawing Figures

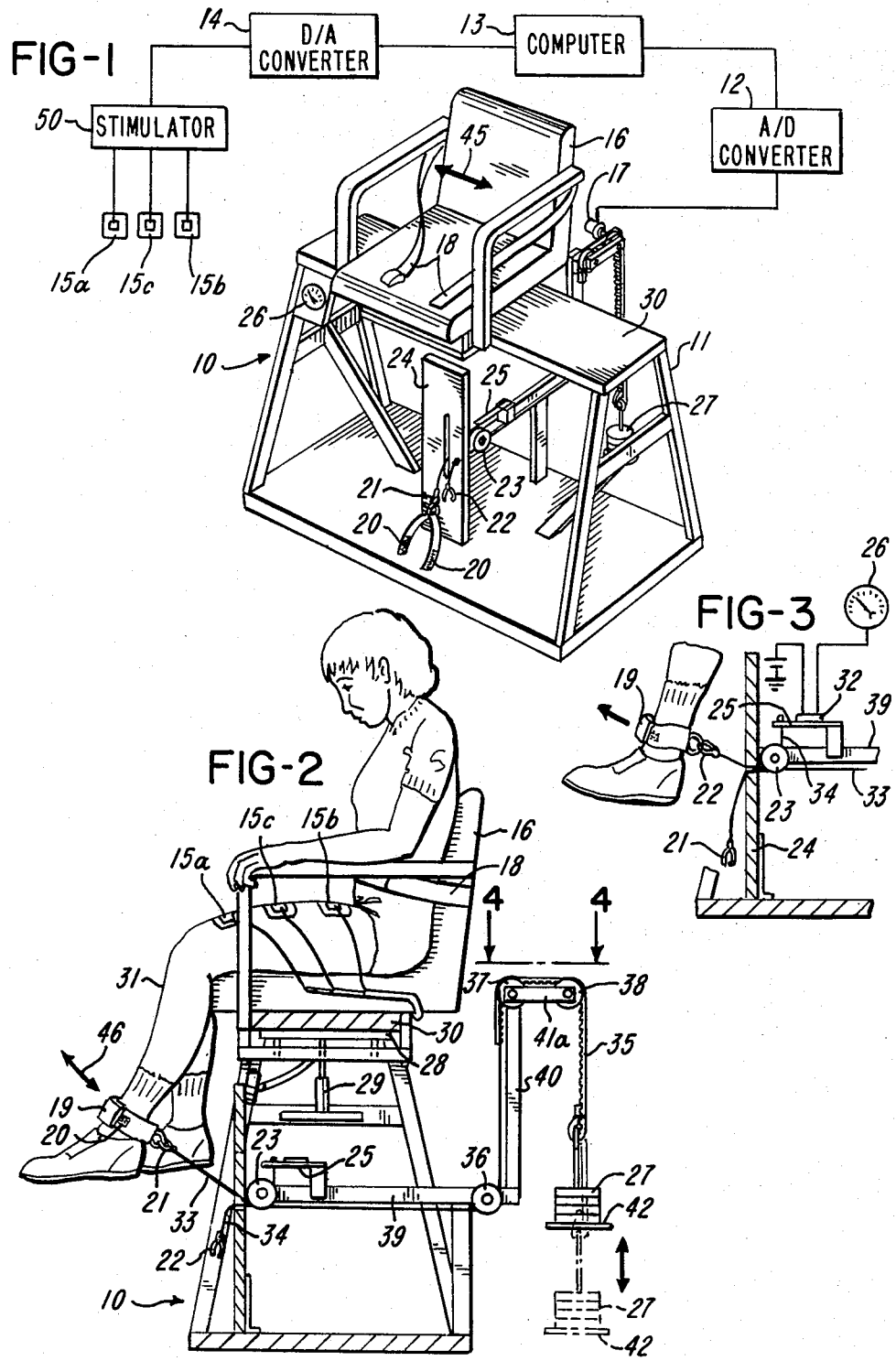

METHOD AND APPARATUS FOR PROVIDING FEEDBACK-CONTROLLED MUSCLE STIMULATION

BACKGROUND OF THE INVENTION

The present invention relates to a method and apparatus for electrically stimulating muscle and, more particularly, to a computer controlled method and apparatus for monitoring muscular activity and adjusting an electrical stimulus to provide controlled and sustained isokinetic contractions. Still more particularly the present invention relates to a method and apparatus for directing coordinated movement of several muscles and exercising them through a specific exercise routine having therapeutic applications in the treatment of paralysis.

The invention which is disclosed and claimed herein has particular value in the treatment of persons who have suffered injuries resulting in spinal cord damage. This particular type of damage often times produces partial or total paralysis of muscles which are controlled from a point below the point of spinal cord damage. The victim then faces a life of relative inactivity and deterioration of muscles which otherwise would be active. It has now been found in accordance with this invention that such muscles can be stimulated to engage in an exercise program once thought to be impossible. Moreover, it has been found that such an exercise program can restore normal muscle tone, even after years of inactivity.

Since the work of Galvani in 1791, it has been known that electricity can be used to induce muscle contractions. Recently, there has been increased awareness of the value of electrostimulation in muscle therapy.

Numerous devices and techniques have been developed for supplying electrical pulses as part of a therapeutic regime of muscle stimulation. Several examples of these are found in the patent literature. Radwan, U.S. Pat. No. 3,387,147 (1968) discloses a muscle stimulating pulse generator designed to provide a pulse signal having a relatively high voltge-to-width ratio and a steep rising wavefront.

Maurer, U.S. Pat. No. 3,817,254 (1974), discloses a transcutaneous stimulator for use in suppressing pain designed to differentially stimulate touch versus pain nerve fibers in an effort to reduce the prickly sensation known to accompany some pain therapy. Maurer notes that differences in the response of nerves to electrostimulation can be used to selectively stimulate different types of nerves. According to Maurer, nerve fibers are distinguished in terms of their size and conduction velocity. He notes that the amplitude of electrical stimulation required to elicit a muscle response increases as the fiber size decreases.

Nawracaj et al, U.S. Pat. No. 4,071,033 (1978), discloses an electrostimulation device which utilizes a heterodyne effect to produce an otherwise painful low frequency stimulus in a muscle and cause the muscle to contract and relax at a low frequency.

Wyss et al, U.S. Pat. No. 4,148,321 (1979), discloses a muscular therapy similar in some respects to Nawracaj et al wherein muscles are made to rhythmically contract and relax at a very low frequency which is induced by modulating a medium frequency current between 3,000 and 100,000 Hz with a low frequency current less than 1 Hz. In one embodiment Wyss et al uses a phase shifter to transform the modulated output current into a three phase current, which is delivered to three electrodes angularly spaced about a limb to provide deep uniform stimulation.

Kofskey et al, U.S. Pat. No. 4,177,819 (1979), teaches an apparatus for stimulating a muscle for 2 to 20 seconds at 2 to 50 second intervals using a 2000 to 3000 Hz signal modulated at 40 to 50 Hz. In one embodiment, the muscle stimulating waveform is controlled by a microprocessor which gradually increases and decreases the amplitude of the stimulation at the beginning and end of each pulse. The microprocessor responds to signals from a no-load/overload sensor and to a manually controlled gain setting signal.

It can be seen that the efforts embodied in the foregoing patents focus on the stimulus itself as the therapeutic agent and have as a principal objective to optimize the intensity, duration and frequency of the stimulus to enhance its therapeutic effects. In the disclosed therapies, the muscle is not stimulated against a load. These prior art systems do not provide smooth isometric contractions and do not respond to muscle activity response to muscle activity in these prior systems.

In order to train a muscle and make it physically strong, it is necessary to work the muscle against a load while producing powerful, sustained, isokinetic contractions at a substantial proportion of the muscle's strength. Isokinetic contractions cannot be maintained for prolonged periods of time in the aforementioned therapies, because they stimulate the muscle synchronously using frequencies much higher than normal physiological frequencies. This causes the muscle to fatigue rapidly, making it impossible to maintain muscle tension.

It has been found that considerable insight regarding the response of human muscles to electric stimulation may be gained by experimentation with cats. The present inventors began their work by such a program, and the results thereof are described in the technical literature. See for instance Petrofsky and Phillips "Microprocessor Controlled Stimulation in Paralyzed Muscle", IEEE NAECON Record (1979), 198–210 and other articles cited therein, all of which are herein incorporated by reference.

SUMMARY OF THE INVENTION

It is an object of the present invention to provide a method and apparatus for electrically stimulating a muscle and exercising the muscle through a specific exercise routine based upon feedback control.

It is another object of this invention to provide apparatus and method for stimulating a human muscle to contract against a dynamic load.

It is still another object of the invention to provide improved apparatus and method for stimulating contraction of a human muscle.

These and other objects of the present invention are accomplished through use of a stimulation device which generates a pair of stimulation signals comprising alternately generated pulses of stimulation energy. The stimulation signals are applied across pairs of electrodes which are preferably adhered to the skin immediately above a muscle to be stimulated. Alternatively, the stimulation signals may be applied to electrode pairs which are implanted in the body.

In the preferred embodiment the stimulation apparatus is controlled through a digital to analog converter by a digitally controlled microprocessor. The limb which is moved by the stimulated muscle is secured against a dynamic load which yieldingly resists movement of the muscle. A feedback sensor senses the movement actually achieved by the limb and transmits an indication thereof through an analog to digital converter back to the microprocessor.

In an exercise routine according to the present invention, a plurality of transcutaneous stimulators are applied to the skin of the subject in a pattern for stimulating a muscle which is connected for moving the limb to be exercised. The stimulators are then excited by a plurality of stimulation signals having profiles for causing the muscle to contract and produce a predetermined movement of the limb. While the limb is contracting, a resisting force is applied thereagainst to cause exertion of the muscle during its contraction. The movement of the limb is sensed and a corresponding feedback signal is generated. The feedback signal is monitored to determine when a predetermined movement has been achieved. After the predetermined movement has been achieved, the stimulation signals are altered to permit the limb to return to its initial position. The process is then repeated to produce an exercise routine.

BRIEF DESCRIPTION OF THE DRAWINGS

FIG. 1 is a schematic illustration of exercising apparatus in accordance with the present invention;

FIG. 2 is a side elevation view of an exercise chair;

FIG. 3 is an illustration of means for indicating the isometric load developed by a human leg;

DESCRIPTION OF THE PREFERRED EMBODIMENT

Figure 4:
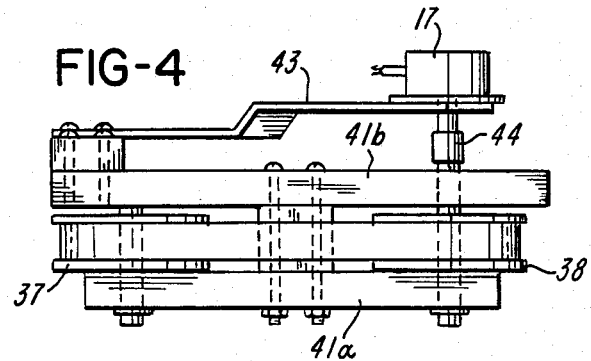
FIG. 4 is a view taken along line 4—4 of FIG. 2.

FIG. 1 illustrates an exercise system 10 constructed in accordance with this invention. The exercise system may comprise a chair 16 mounted on a support frame 11. Chair 16 rests upon a support board 30 and is clamped in place by a clamp 28, as illustrated in FIG. 2. Clamp plate 28 may be forced upwardly against the lower surface of support board 30 by any convenient means, such as, for instance, a rotary handle and screw arrangement 29. When clamp 28 is released chair 16 may be moved along the surface of support board 30 as illustrated by the arrow 45. This enables positioning of chair 16 for accommodating an exercise routine for either the left leg or the right leg of a person seated in chair 16.

Exercise system 10 also comprises a seat belt 18 for securing a person in chair 16 and a leg strap 19 for grasping the lower portion of a leg 31. Leg strap 19 is provided with interlocking pieces of hook and loop fastening fabric 20, 20 of the type sold by Velcro U.S.A., Inc. of New York, N.Y. under the trademark VELCRO. Thus leg strap 19 be easily and securely fastened around a leg of any size.

Leg strap 19 has a steel eyelet for fastening to one or the other of a pair of scissor-type eyelet fasteners 21, 22. Fasteners 21 and 22 are attached to pair of cables 33, 34, respectively, which extend through a facing board 24.

Cables 33 and 34 are guided by a roller 23 having a pair of offset guide channels (not illustrated). Cable 33 extends rearwardly from roller 23 around a roller 36 and thence upwardly for attachment to a toothed belt 35. Cable 34 wraps around roller 23 and extends upwardly for attachment to a relatively stiff bending arm 25 supported upon frame member 39, as best illustrated in FIG. 3.

Toothed belt 35 extends around a pair of toothed rollers 37 and 38 mounted between a pair of support plates 41a and 41b, as best illustrated in FIG. 4. Support plates 41a and 41b are securely supported by frame member 40, which in turn is supported by frame member 39.

Belt 35 supports a set of weights placed upon a pan 42. Thus when the leg 31 moves arcuately as indicated by arrow 46, the weights 27 are raised or lowered. The arrangement provides a dynamic load which resists but does not prevent movement of leg 31.

When the leg 31 is extended upwardly, pulling cable 33 and belt 35, the movement is measured by a potentiometer 17 (see FIG. 4) attached to roller 38 by a coupling device 44. The housing for potentiometer 17 is supported by a support arm 43 secured to the upper support plate 41, as viewed in FIG. 4.

As the leg 31 moves and pulls belt 35 across roller 38, the potentiometer 17 transmits a feedback signal to A/D converter 12. A/D converter 12 converts the feedback signal into a digital format for processing by computer 13, as hereinafter described in detail. Computer 13 responds to the feedback signal by transmitting a digital control signal to D/A converter 14. D/A converter 14 then generates an analog stimulation signal for stimulator 50. Stimulator 50 uses the control signal from D/A converter 14 for generation of a pair of stimulation signals which are applied across electrodes 15a, 15b and 15c. Electrodes 15a, 15b and 15c are commercially available transcutaneous electrodes such as MEDTRONIC Model 3793 electrodes sold by Medtronic, Inc. of Minneapolis, Minn.

For an exercise as hereinafter described the electrodes are placed in spaced positions above the quadriceps muscles of one leg, as generally illustrated in FIG. 2. The electrodes are attached to the leg of the subject by hypoallerqenic tape or elastic bandages. Prior to application of the electrodes, the skin is cleaned and dried. An electrode gel, such as TENS electrode gel, also sold by Medtronic, Inc. is applied to the electrodes before they are placed upon the skin of the subject.

When the stimulation signals from stimulator 50 are applied to electrodes 15a, 15b and 15c the quadriceps muscles of the subject are stimulated to contract and raise the leg 31 against the dynamic resistance of cable 33 as described above. Alternatively, leg strap 19 may be connected to cable 34 in which case leg 31 strains isometrically against bending arm 25. This produces an output signal from a strain gauge 32 mounted on top of bending arm 25. Strain gauge 32 is connected to provide a load signal for a meter 26 which may be mounted at any convenient location. The meter 26 provides a "strength" indication for use in the exercise procedure hereinafter described in detail.

Figure 7:
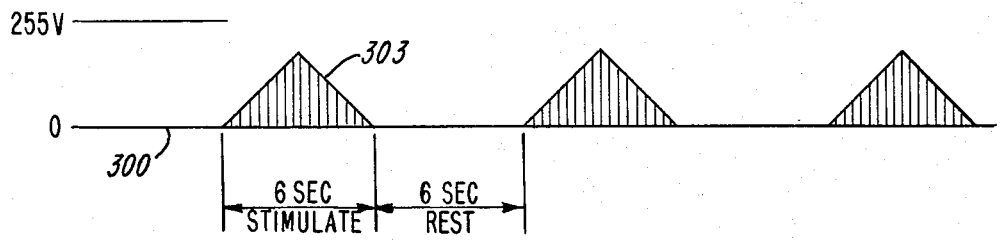
FIG. 7 is a schematic illustration of a stimulation signal.
Figure 8:
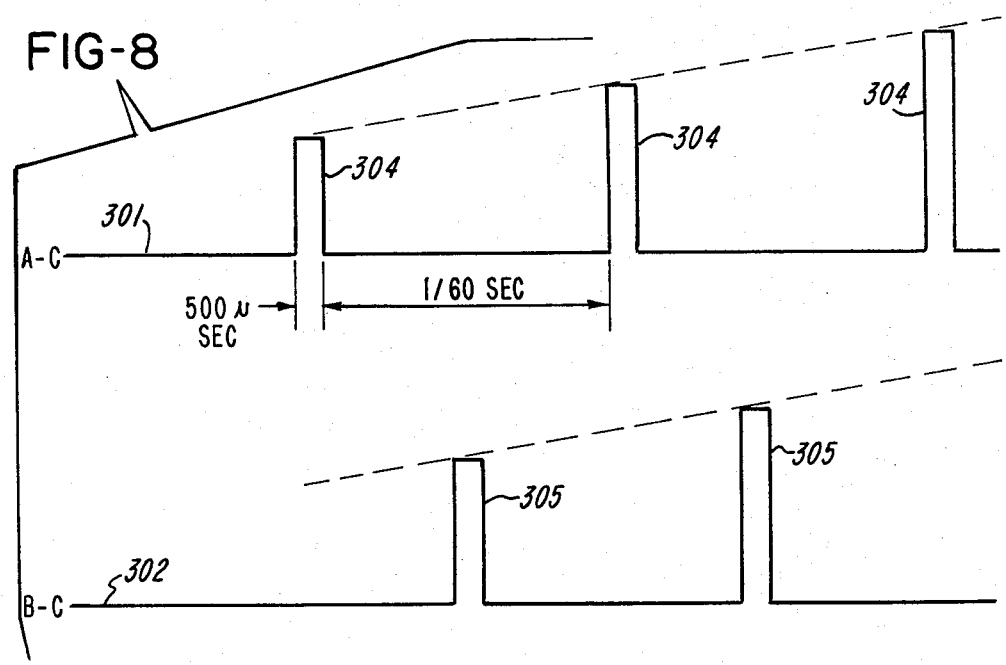
FIG. 8 is an enlarged schematic illustration of portions of two alternately pulsed stimulation signals.

The stimulation signals which are applied to electrodes 15a, 15b, and 15c are illustrated in FIGS. 7 and 8. Stimulator 50 generates a first signal 301 as illustrated by the top line of FIG. 8 and a second signal 302 as illustrated by the bottom line of FIG. 8. Signal 301 is applied across terminals 15a and 15c, while signal 302 is applied terminals 15b and 15c. Terminal 15c is connected to high voltage ground, as hereinafter described with reference to FIG. 5.

Each of signals 301 and 302 has an envelope generally illustrated by triangular projections 303 rising above the line 300 of FIG. 7. The signal is characterized by alternating stimulation and rest periods of approximately 6 seconds each. During the stimulation period the signal is pulsed at a frequency in a range from about 55 to 65 Hz and preferably about 60 Hz. The pulses which are so generated have peak values which increase gradually from a value near 0 volts to a maximum which is somewhat less than 255 volts and which produces maximum effort from the muscle or muscle group being stimulated. Thereafter the pulse amplitudes decrease gradually to a value near zero, and the muscle is rested. The maximum voltage value depends upon the state of exhaustion of the muscle and the effort which is desired. As the muscle tires, more stimulation voltage is required for production of the same effort. Generally speaking a maximum voltage of about 255 volts produces recruitment of all motor units and results in maximum effort by the muscle.

As shown in FIG. 8, signal 301 comprises a series of pulses 304 while signal 302 comprises another series of pulses 305. Pulses 304 and 305 are generated in an alternating sequence at a frequency of 60Hz each. Thus the effective combined frequency is 120Hz. Pulses 304 and 305 have peak values which conform with the signal enevelope of FIG. 7. They have a duration of approximately 500 microseconds, so that each of signals 301 and 302 has a duty cycle of 0.03. It has been found that if the pulse width is increased, then the stimulation voltage may be decreased and vice versa.

Figure 5:
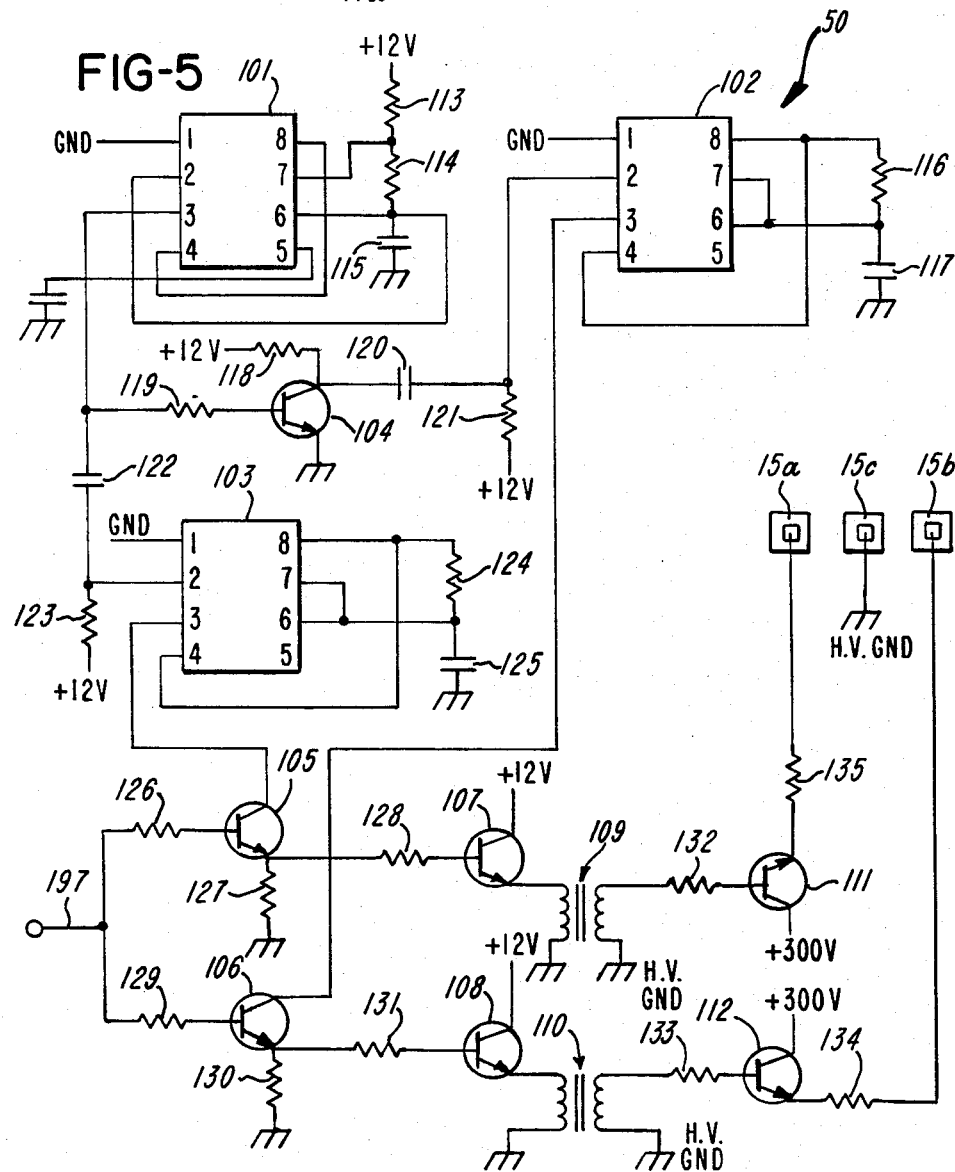
FIG. 5 is a schematic illustration of a stimulation apparatus.

The circuitry for producing signals 301 and 302 is illustrated in FIG. 5. The associated feedback and control circuitry is illustrated schematically in FIG. 6. The circuitry includes integrated circuits as identified in Table I and components as identified in Table II. Table III lists significant pin number designations for the principal integrated circuits listed in Table I.

TABLE I

| Ref. Numeral | Integrated Circuits Circuit Type |
|---|---|
| 12 | ADCO808 (National Semiconductor) |
| 13 | DAC0831 (National Semiconductor) |
| 101 | SE/NE 555 (Signetics) |
| 102 | SE/NE 555 (Signetics) |
| 103 | SE/NE 555 (Signetics) |
| 201 | SN74LS138 (Texas Instruments) |
| 204 | SE/NE 555 (Signetics) |
| 205 | 1/6 7404 |
| 206 | 1/2 LM1458 |
| 207 | 1/6 7404 |
| 208 | 1/6 7404 |
| 209 | 1/2 LM1458 |
| 210 | 1/2 LM1458 |
| 211 | 1/2 LM1458 |
| 212 | 1/2 LM1458 |
| 213 | 1/2 LM1458 |
| 214 | 1/2 LM1458 |

TABLE II

| Components | |
|---|---|
| Ref. Numeral | Identification |
| 104 | 2N3904 |
| 105 | 2N3904 |
| 106 | 2N3904 |
| 107 | 2N3904 |

TABLE II-continued

| Components | |
|---|---|
| Ref. Numeral | Identification |
| 108 | 2N3904 |
| 111 | 2SC1308 |
| 112 | 2SC1308 |
| 113 | 100k |
| 114 | 100k |
| 115 | 0.1 μf |
| 116 | 10k |
| 117 | 0.1 μf |
| 118 | 10k |
| 119 | 10k |
| 120 | 0.001 μf |
| 121 | 22k |
| 122 | 0.001 μf |
| 123 | 22k |
| 124 | 10k |
| 125 | 0.1 μf |
| 126 | 470Ω |
| 127 | 10k |
| 128 | 470Ω |
| 129 | 470Ω |
| 130 | 10k |
| 131 | 470Ω |
| 132 | 1k |
| 133 | 1k |
| 134 | 100Ω |
| 135 | 100Ω |
| 136 | 0.1 μf |
| 219 | 39 μf |
| 220 | 10 μf |
| 221 | 100k |
| 222 | 330k |
| 223 | 680k |
| 234 | 100k |
| 235 | 82k |

TABLE III

| | Pin Functions | | |
|---|---|---|---|
| Component | Pin No | Function Name | Function |
| Slot #3 of Apple Computer | 1 | I/O SELECT | LO during slot #3 addressing |
| | 2 | A0 | Address bit 0 |
| | 3 | A1 | Address bit 1 |
| | 4 | A2 | Address bit 2 |
| | 7 | A5 | Address bit 5 |
| | 8 | A6 | Address bit 6 |
| | 9 | A7 | Address bit 7 |
| | 18 | R/$\overline{W}$ | Buffered Read/Write signal |
| | 25 | +5V | +5 volts |
| | 26 | GND | ground |
| | 33 | −12v | −12 volts |
| | 40 | O | phase 0 clock |
| | 42 | D7 | Data bit 7 |
| | 43 | D6 | Data bit 6 |
| | 44 | D5 | Data bit 5 |
| | 45 | D4 | Data bit 4 |
| | 46 | D3 | Data bit 3 |
| | 47 | D2 | Data bit 2 |
| | 48 | D1 | Data bit 1 |
| | 49 | D0 | Data bit 0 |
| | 50 | +12v | +12 volts |
| SN74LS138 | 1 | A | select line |
| | 2 | B | select line |
| | 3 | C | select line |
| | 4 | G2A | enable line |
| | 5 | G2B | enable line |
| | 6 | G1 | enable line |
| | 10 | Y5 | output line |
| | 12 | Y3 | output line |
| | 14 | Y1 | output line |
| ADC 0808 | 3 | In5 | analog inut #5 |
| | 6 | start | start strobe |
| | 8 | D3 | Data bit 3 |
| | 9 | out enable | output enable |
| | 10 | clock | clock |

TABLE III-continued

| Component | Pin No | Function Name | Function |
|---|---|---|---|
| | 14 | D1 | data bit 1 |
| | 15 | D2 | data bit 2 |
| | 17 | D0 | data bit 0 |
| | 18 | D4 | data bit 4 |
| | 19 | D5 | data bit 5 |
| | 20 | D6 | data bit 6 |
| | 21 | D7 | data bit 7 |
| | 23 | Add C | address bit C |
| | 24 | Add B | address bit B |
| | 25 | Add A | Address bit A |
| | 27 | In 1 | analog input #1 |
| | 28 | In 2 | analog input #2 |
| DAC 0831 | 1 | $\overline{CS}$ | input latch |
| | 2 | $\overline{WR_1}$ | data load |
| | 4 | $DI_3$ | digital input bit 3 |
| | 5 | $DI_2$ | digital input bit 2 |
| | 6 | $DI_1$ | digital input bit 1 |
| | 7 | $DI_0$ | digital input bit 0 |
| | 9 | $R_{fb}$ | zero adjustment |
| | 11 | $I_{out\,1}$ | output proportional to digital input |
| | 12 | $I_{out\,2}$ | output proportional to complement of digital input |
| | 13 | $DI_7$ | digital input bit 7 |
| | 14 | $DI_6$ | digital input bit 6 |
| | 15 | $DI_5$ | digital input bit 5 |
| | 16 | $DI_4$ | digital input bit 4 |
| | 19 | $I_{LE}$ | chip select |

The operation of stimulator 50 will now be described with reference to FIG. 5. That figure shows 3 integrated circuits 101, 102, and 103 of identical construction. These are timing circuits such as Signetics 555 timers. IC 101 is connected to operate as a 60 Hz free running multivibrator. The output from IC 101 is applied via transistor 104 to input pins 2 of IC 102 and 103. IC 102 and 103 produce alternating 500 microsecond pulses each at a frequency of 60 Hz for application to the collector terminals of transistors 105 and 106. The pulse width is set by appropriate selection of the resistance for resistors R116 and R124 and the capacitance of capacitors 117 and 125, as shown in the manufacturer's data sheets for integrated circuits 102 and 103. The phase between the pulses produced by integrated circuits 102 and 103 is set by appropriate selection of the resistance for resistors 113 and 114.

An analog voltage representing the desired envelope for the stimulation pulses is applied to input line 197, which is connected to the base terminals of transistors 105 and 106. Concomitantly, output pulses from pin 3 IC of 102 and pine 3 of IC 103 are applied to the collectors of transistors 106 and 105 respectively. As a result thereof transistors 106 and 105 generate emitter currents across resistors 130 and 127 providing voltage profiles of the general shape illustrated in FIGS. 7 and 8. These voltages are applied to the base terminals of transistors 108 and 107. This results in corresponding voltage pulses ranging between 0 and 12 volts across the primary windings of transformers 110 and 109.

The voltage pulses across the primary windings of transformers 110 and 109 produce low current, high voltage pulses ranging from 0 to 255 volts across the secondary windings of transformers 110 and 109. The secondary windings of transformers 110 and 109 have one side grounded to a high voltage ground which is different from the ground utilized for the primary windings thereof. The output pulses from the secondary windings are thereby RF isolated to maintain the safety of the person who is the subject of the exercise procedure.

Figure 6:
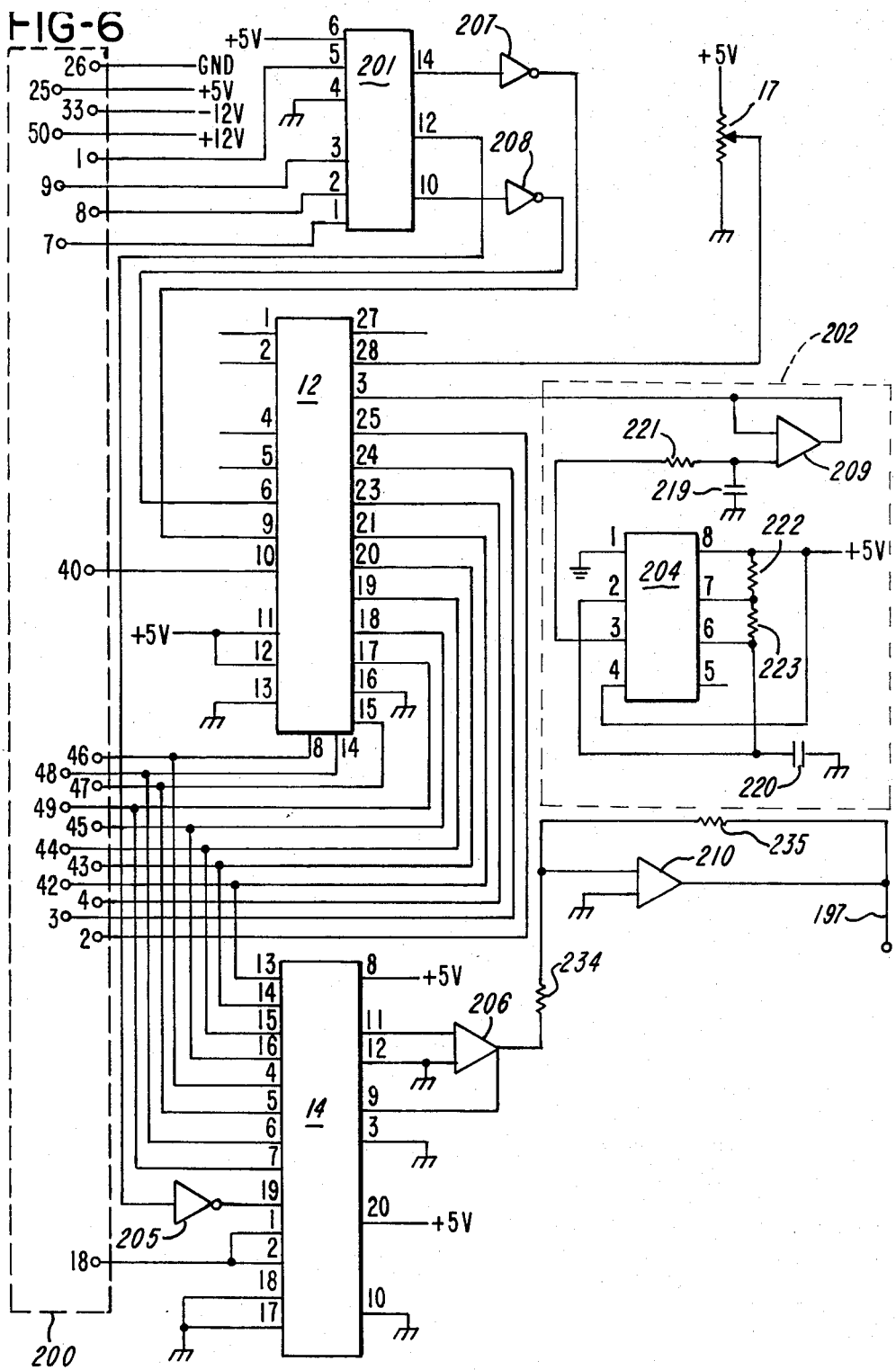
FIG. 6 is a schematic illustration of a control system for the stimulation apparatus of FIG. 5.

Output voltage pulses from transformers 110 and 109 are applied to the base terminals of transistors 112 and 111 respectively. Transistors 112 and 111 provide a current gain so as to have high current, high voltage and low duty cycle pulses available for application across terminal pairs 15a–15c and 15b–15c. The analog driving signal appearing at line 197 is generated by the control system circuitry as illustrated in FIG. 6.

The heart of the control system is the computer 13, which in the embodiment described herein is an APPLE II computer sold by Apple Computer Inc. of Cupertino, Calif. The APPLE II computer is provided with several slots into which may be plugged connectors for customized peripheral devices. The system described herein is plugged into slot number 3, which includes a connector 200 as illustrated by dotted lines in FIG. 6. The computer addresses analog to digital converter 12 and digital to analog computer 13 through a decoder/demultiplexer 201. The peripheral board is addressed by the computer in memory locations C100 to C1FF (hexadecimal notation). Pin number 1 of connector 200 provides a signal from the computer's input/output select line. This line becomes active whenever one of the memory locations C1FF to C100 are selected for memory read or write operations. Pin number 1 is tied to pin number 5 of IC 201, an SN74LS138 integrated circuit. Pin number 5 is the G2 input of IC 201. A signal at this terminal enables IC 201 to decode the three high order bits (A7, A6, and A5) of an eight-bit address provided by the computer. These three bits appear at pin numbers 9, 8 and 7 respectively of connector 200.

IC 201 is designed for producing eight decoded outputs, but only three of these outputs are used. These outputs appear at pin numbers 14, 12 and 10 and respectively read A/D converter 12, strobe D/A converter 14 and strobe A/D converter 12. A/D converter 12 is an eight channel device sold by National Semiconductor under the designation ADC0808. A/D converter 12 receives its clock from the system clock on pin number 40 of connector 200.

When a strobe signal appears at pin number 12 of IC 201, A/D converter 12 is enabled for reading and digitizing analog signals appearing at any one of eight analog input ports (only two of which are used). The two analog input ports are addressed by a three-bit address appearing at pin numbers 25, 24 and 23 of A/D converter 12. The three address bits are the three least significant bits of an eight-bit address generated by computer 13. These three bits appear at pin numbers 2, 3 and 4 of connector 200 (the three most significant bits appearing at pin numbers 7, 8 and 9 as above stated and bit numbers 3 and 4 not being utilized.

Computer 13 generates the above mentioned eight-bit address whenever any one of computer memory address locations 50080 to 50087 (decimal notation) are strobed. Such strobing not only generates an associated eight-bit address, but also enables A/D converter 12 by causing generation of a strobe signal at output pin 12 of IC201, as above described. Memory locations 50080 to 50087 are strobed by execution of a "POKE" instruction, such as, for instance, the instruction "POKE 50080,0" appearing at line number 1450 of the computer program set forth in TABLE IV hereof.

As mentioned above, the described embodiment supplies only two analog input signals for digitizing by A/D converter 12. These two signals appear at pin numbers 3 and 28 of A/D converter 12 and are addressed respectively by "POKING" memory locations 50080 and 50082 respectively. The resulting digitized representation thereof appears in eight-bit format at pin numbers 17, 14, 15, 8, 18, 19, 20 and 21 of A/D converter 12. These eight bits are read into memory location 49952 (decimal notation) upon execution of a "PEEK" instruction.

It is therefore seen that when memory addresses 50080 through 50087 are strobed, the conputer selects the analog channel which is to be multiplexed into A/D converter 12. Simultaneously with this selection A/D converter 12 is strobed to start conversion of the analog signal to digital format. A maximum of 100 microseconds is required for the analog to digital conversion, after which the computer may execute a normal memory read cycle, whereby the digitized data is transferred onto the data bus and stored in memory location 49952. It is to be noted that the output of A/D converter 12 is a eight-bit binary signal ranging between values of 0 and 255 (decimal) for analog input voltages between 0 and 5 volts.

The analog signal supplied to pin No. 3 of A/D converter 12 has a triangular voltage profile and is produced by a profile generating circuit 202, comprising IC 204, amplifier 209, capacitors 219 and 220, and resistors 219 through 223. IC 204 generates a square wave at 1/6 Hz which is converted to a triangular ramp by capacitor 219 and resistor 221 and is buffered by amplifier 209. The triangular voltage profile, so generated, represents a desired response from potentiometer 17 when the leg of the subject is being stimulated to raise and lower.

The output of potentiometer 17 is applied to pin No. 28 of A/D converter 12, as shown in FIG. 6. An output of 5 volts from potentiometer 17 represents a shaft angle rotation of 360°. The diameter of roller 38 is selected such that one rotation thereof corresponds to a leg movement of about 70 degrees from its initial vertial position.

The amplitude of the analog stimulation signal appearing at line 197 is controlled by D/A converter 14, a DAC0831 integrated circuit sold by National Semiconductor. D/A converter 14 is selected for operation by applying a strobe signal to pin 19 thereof. Also, a write signal (logic LO) is applied to input terminals 1 and 2 for activating the transfer of data to the internal latch register of D/A converter 14. The data so transferred is an eight-bit stimulation command code appearing at terminals 13, 14, 15, 16, 4, 5, 6 and 7 of D/A converter 13. The output of D/A converter 14 is buffered and amplified and thereafter applied to input line 197 of stimulator 50.

Computer 13 generates eight-bit binary representation of stimulation command voltages ranging between 0 and 255 by executing an appropriate POKE instruction. A desired stimulation voltage ranging between 0 and 255 is POKED into memory location 50016 (decimal). When this memory location is POKED the computer generates an address for IC201 which causes output pin 12 to go LO. This LO output signal is inverted by inverter 205 to create the above mentioned strobe signal for D/A converter 14.

The computer program for producing the above described operation is described in the program listing set forth in TABLE IV. This program is written in source code in accordance with the APPLESOFT variation of the well known BASIC language. The program will be self-explanatory to persons skilled in the art and only brief comments need be made.

The program set forth in TABLE IV includes an isometric strength measurement routine beginning at line 220 and a main control program beginning at line 1000. The main control program includes a start cycle beginning at line 1250 and a muscle stimulation routine beginning at line 1432. The start cycle finds the beginning of a ramp generated by the profile generator 202.

During the isometric measurement routine the computer increments a variable Y from 1 to 17 (line 290) and POKES the value 10Y into memory location 50016. This causes generation of stimulation pulses having a voltage equal to the value 10Y. When the muscle begins to develop tension, then the test supervisor depresses the Escape key on the computer control board. This action loads the ASCII code 155 into memory location 49152. The computer checks that memory location at line 329 and jumps to line 400 if the Escape key has been depressed. The computer then assigns the current value of 10Y to the variable Z as a threshold voltage.

After the threshold voltage has been established, the computer enters the main control program to determine the maximum strength of the muscle by isokinetic exercise. During this routine the computer steps the stimulation voltage from the value Z up to 255 volts in 10 volt steps (lines 1045 and 1060). During this period of time the leg is attached to cable 34 as indicated by FIG. 3. When strength meter 36 indicates that the strength has leveled off, then the test supervisor again depresses the Escape key. The computer checks memory location 49152 once during each voltage step (line 1105) and proceeds to line 1120, if the Escape key has been depressed.

After the maximum strength has been determined, the computer looks for a start of a cycle (line 1250).

The isokinetic exercise routine begins at line 1432. During this routine the computer generates stepped variations for a variable Z9 and POKES the value of Z9 into memory location 50016. After each new value of Z9 has been utilized for generation of a corresponding stimulation voltage, the computer checks to see if Z9 has a value equal to 255 (maximum stimulation voltage). If that value is noted, then the isokinetic exercise routine is terminated. If not, the computer proceeds to execute the instructions at line 1450 which cause reading of the analog voltages generated by profile generator 202 and potentiometer 17. These voltages are digitized and utilized to establish values for variables A8 and A9 respectively.

If A8 is greater than A9, the computer knows that the leg is not raised as much as it should be, and the value of Z9 is increased. This then increases the stimulation voltage command generated by the computer. Conversely, if A8 is less than A9, Z9 and the stimulation command are decreased. When A8 has decreased to a value indicating the end of a cycle, then the leg is rested for the duration of a counting loop which continues for approximately 6 seconds.

It will be appreciated that the muscular response produced by the invention herein described is not limited to the use of transcutaneous stimulators. Stimulation signals of the general type herein described may be applied (at greatly reduced voltage levels) to implanted sleeve electrodes which surround the motoneurons as described in the Petrofsky article.

While the method herein described and the form of apparatus for carrying this method into effect constitutes preferred embodiments of this invention, it is to be understood that the invention is not limited to this precise method and form of apparatus, and that changes may be made in either without departing from the scope of the invention which is defined in the appended claims.

TABLE IV

| | |
|---|---|
| 1 | POKE 50016,10 |
| 2 | REM Z = THRESHOLD VOLTAGE |
| 3 | REM STRENGTH=MAXIMUM VOLTAGE LEVEL |
| 4 | REM K3=LOW GAIN CAL . . . K2 =HIGH GAIN CAL |
| 5 | REM G3=REAL STRENGTH |
| 6 | K3 = .05:K2 = 1 / 46 |
| 7 | DIM A(1000) |
| 10 | REM ********************************* |
| 20 | REM EXERCISE 1 PROGRAMS |
| 30 | REM ********************************* |
| 40 | REM |
| 50 | REM |
| 51 | POKE 50016,10 |
| 100 | FOR X = 1 TO 30: PRINT : NEXT X |
| 110 | PRINT "THIS PROGRAM STIMULATES": PRINT " THE QUADRICEPS MUSCLE" |
| 120 | PRINT : PRINT : PRINT |
| 125 | PRINT "SET UP DYNAMOMETER FOR ISOMETRICS": PRINT : PRINT |
| 130 | PRINT "CONNECT LEADS TO SUBJECT NOW" |
| 140 | PRINT : PRINT "BLACK LEAD TO CENTER" |
| 150 | PRINT |
| 160 | PRINT "TYPE OR WHEN READY" |
| 170 | INPUT A$ |
| 180 | IF A$ = "GO" THEN 200 |
| 190 | GOTO 160 |
| 200 | PRINT : PRINT : PRINT : PRINT : PRINT : PRINT : PRINT |
| 210 | FOR I = 1 TO 25: PRINT : NEXT I |
| 220 | PRINT "MEASUREMENT OF ISOMETRIC STRENGTH" |
| 230 | PRINT : PRINT : PRINT : PRINT |
| 240 | PRINT "DEFINE THRESHOLD": PRINT |
| 250 | PRINT " TO DETERMINE THE THRESHOLD": PRINT "WATCH THE MUSCLE AND NOTE": PRINT "WHEN THE MUSCLE STARTS TO ": PRINT "CONTRACT" |
| 260 | PRINT "TYPE ESC WHEN THE MUSCLE DEVELOPS": PRINT "TENSION" |
| 270 | PRINT : PRINT "THRESHOLD WILL BE PRINTED": PRINT "AT THE END" |
| 271 | PRINT : PRINT "SET DYNAMOMETER TO ZERO": PRINT "TURN ON STIMULATOR" |
| 275 | PRINT : PRINT : FLASH : PRINT " CONTROL C TO STOP AND SWITCH": NORMAL |
| 280 | PRINT : PRINT "TYPE ANY KEY TO START": INPUT S$ |
| 283 | PRINT : PRINT : FLASH |
| 284 | NORMAL |
| 285 | FOR H = 1 TO 300:U = SIN (H): NEXT H |
| 290 | FOR Y = 1 TO 17 |
| 295 | PRINT "VOLTAGE LEVEL=";Y * 10 |
| 300 | FOR I = 1 TO 150 |
| 310 | POKE 50016,Y * 10 |
| 320 | NEXT I |
| 325 | POKE 50016,10: FOR H = 1 TO 300: NEXT H |
| 329 | G1 = PEEK (49152): IF G1 = 155 THEN GOTO 400 |
| 330 | NEXT Y |
| 400 | Z = Y * 10 − 10: PRINT : PRINT "THRESHOLD WAS ";Y * 10 |
| 401 | POKE 49168,0 |
| 410 | FOR X = 1 TO 1000: NEXT X |
| 411 | FOR X = 1 TO 3000: NEXT X |

TABLE IV-continued

| | |
|---|---|
| 500 | FOR H = 1 TO 700: NEXT H |
| 550 | FOR I = 1 TO 30: PRINT : NEXT I |
| 599 | INVERSE : PRINT "ISOKINETIC EXERCISE" |
| 600 | REM |
| 601 | NORMAL |
| 610 | FOR I = 1 TO 10: PRINT : NEXT I |
| 620 | FOR I = 1 TO 700: NEXT I |
| 621 | FOR I = 1 TO 2000: NEXT I |
| 699 | GOTO 1000: REM ***RE ACTIVATE FOR VARIABLE SPEED CONTRACTIONS BY REMOVING THIS LINE****************** |
| 700 | PRINT "WHAT VELOCITY DO YOU WANT" |
| 710 | PRINT : PRINT : PRINT |
| 720 | PRINT "ENTER S FOR SLOW AND F FOR FAST": PRINT : PRINT : PRINT |
| 730 | INPUT D$ |
| 740 | IF D$ = "S" THEN GOTO 800 |
| 750 | IF D$ = "F" THEN GOTO 900 |
| 760 | PRINT "NON LEGAL INPUT ....TRY AGAIN": GOTO 710 |
| 800 | REM START SLOW ROUTINES |
| 805 | R = 3 |
| 810 | LET VEL = R |
| 850 | GOTO 1000 |
| 900 | REM START FAST ROUTINES |
| 905 | R = 50 |
| 910 | LET VEL = R |
| 950 | GOTO 1000 |
| 1000 | REM MAIN CONTROL PROGRAM |
| 1010 | POKE 50016,10 |
| 1020 | REM DETERMINE STRENGTH |
| 1030 | FOR I = 1 TO 10: PRINT : NEXT I |
| 1040 | PRINT "DETERMINE MAXIMUM STRENGTH OF MUSCLE": PRINT : PRINT : PRINT |
| 1041 | PRINT "WHEN STRENGTH HAS LEVELED OFF": PRINT "TYPE ESC": PRINT : PRINT : FLASH : PRINT "CONTROL C AND SWITCH TO STOP FAST": NORMAL : PRINT |
| 1043 | PRINT : PRINT "TYPE GO TO START": INPUT A$: IF A$ = "GO" THEN GOTO 1044: GOTO 1043 |
| 1044 | REM |
| 1045 | FOR J = Z TO 255 STEP 10 |
| 1046 | PRINT "VOLTAGE LEVEL =";J |
| 1050 | FOR I = 1 TO 100 |
| 1060 | POKE 50016,J |
| 1070 | REM |
| 1080 | NEXT I |
| 1090 | POKE 50016,10 |
| 1100 | FOR U = 1 TO 2000: NEXT U |
| 1105 | G1 = PEEK (49152): IF G1 = 155 THEN GOTO 1120 |
| 1110 | NEXT J |
| 1120 | PRINT : PRINT : PRINT "VOLTAGE LEVEL AT MVC=";J: PRINT : PRINT |
| 1121 | POKE 49168,0 |
| 1130 | STRENGTH = J |
| 1140 | REM STRENGTH = VOLTAGE LEVEL AT MVC |
| 1145 | POKE 49168,0 |
| 1146 | PRINT "WHAT IS THE READING?": INPUT METER: PRINT "INPUT THE GAIN...1 FOR HIGH . . . 2 FOR LOW": INPUT GAIN |
| 1147 | REM |
| 1148 | GOTO 8000 |
| 1149 | FOR I = 1 TO 10: PRINT : NEXT I: GOSUB 5000 |
| 1150 | FOR I = 1 TO 30: PRINT : NEXT I |
| 1155 | FOR I = 1 TO 30: PRINT : NEXT I |
| 1156 | D$ = "" |
| 1157 | PRINT D$; "RUN STIM" |
| 1160 | PRINT "SET UP DYNAMOMETER FOR DYNAMIC" |
| 1170 | PRINT "EXERCISE" |
| 1180 | NORMAL |
| 1190 | FOR I = 1 TO 10: PRINT : NEXT I |
| 1200 | REM |
| 1220 | PRINT "TYPE GO TO CONTINUE" |
| 1230 | INPUT A$ |
| 1240 | IF A$ = "GO" THEN GOTO 1250: GOTO 1220 |
| 1250 | REM LOOK FOR START OF CYCLE |
| 1255 | D9 = 0 |
| 1260 | FOR X = 1 TO 1000 |
| 1265 | POKE 50080,0 |
| 1270 | A(X) = PEEK (49952) |
| 1280 | NEXT X |
| 1290 | G7 = 150 |

TABLE IV-continued

```
1300  FOR X = 1 TO 1000
1310  IF G7 > A(X) THEN G7 = A(X)
1320  NEXT X
1330  POKE 50080,0
1340  G8 = PEEK (49952)
1350  IF G8 < G7 + 5 THEN GOTO 1400
1360  GOTO 1330
1400  REM STIMULATE THE LEG
1405  FLASH : PRINT "TURN OFF POWER THEN
      CONTROL C TO END": NORMAL
1410  PRINT "CONTRACTION ";D9 + 1:D9 = D9 + 1
1420  REM
1430  FOR X = 1 TO 250: NEXT X
1432  REM ********STIMULATE MUSCLE*****
1435  Z9 = Z
1440  POKE 50016,Z9
1441  IF Z9 = 255 THEN GOTO 6000
1450  POKE 50080,0:A8 = PEEK (49952): POKE
      50082,0:A9 = PEEK (49952)
1460  IF A8 > A9 THEN LET Z9 = Z9 + 1
1470  IF A8 < A9 THEN LET Z9 = Z9 - 1
1480  IF A8 < G7 + 3 THEN GOTO 1500
1490  GOTO 1440
1500  POKE 50016,2
1510  FOR I = 1 TO 1000: NEXT I
1520  GOTO 1330
1530  REM
1540  REM
1550  REM
5000  REM **************************
5010  REM THIS SUBROUTINE LISTS STRENGTH AND
      LOAD
5020  REM **************************
5030  REM
5040  PRINT : PRINT "WHAT TYPE OF EXPERIMENT?"
5041  PRINT " 1) FOR NO LOAD"
5042  PRINT " 2) FOR 33% LOAD"
5043  PRINT " 3) FOR 66% LOAD"
5044  PRINT
5050  INPUT TYPE
5055  IF TYPE > 4 THEN GOTO 5040
5056  IF TYPE = 0 THEN GOTO 5040
5057  IF TYPE = 4 THEN GOTO 5040
5060  IF GAIN = 1 THEN GOTO 5100
5070  IF GAIN = 2 THEN GOTO 5200
5080  GOTO 1145
5100  G3 = K2 * METER
5110  GOTO 5500
5200  G3 = K3 * METER
5210  GOTO 5500
5500  PRINT "THE STRENGTH WAS ";G3;" POUNDS"
5510  PRINT
5520  IF TYPE = 1 THEN GOTO 5600
5530  IF TYPE = 2 THEN GOTO 5700
5540  IF TYPE = 3 THEN GOTO 5800
5550  GOTO 1145
5600  PRINT "SET THE LOAD TO NO WEIGHT...": PRINT :
      PRINT "THIS IS A ZERO LOAD EXPERIMENT"
5610  GOTO 5900
5700  PRINT "THE LOAD MUST BE SET AT ";G3 / 3;" LBS"
5710  GOTO 5900
5800  PRINT "THE LOAD MUST BE SET AT ";2 * G3 / 3;"
      LBS": PRINT : PRINT : PRINT : FLASH :
      PRINT "SO . . . SET IT": NORMAL
5810  GOTO 5900
5900  FOR I = 1 TO 300:H = SIN (54): NEXT I
5910  RETURN
6000  REM *END PROGRAM DUE TO FATIGUE*
6005  POKE 50016,2
6010  PRINT : PRINT : PRINT : PRINT : PRINT : PRINT
6020  PRINT "THE MUSCLE IS BEING STIMULATED
      FULLY":
      PRINT "EITHER THE MUSCLE IS FATIGUED OR ":
      PRINT "SOMETHING IS WRONG...END PROGRAM"
6025  PRINT "TYPE " CONT " TO RESUME OR THE
      PROGRAM ENDS"
6026  INPUT A$: IF A$ = "CONT" THEN GOTO 1330
6030  END
8000  REM CHECK FOR BAD ENTRY
8010  IF METER = 0 THEN GOTO 1146
8020  IF METER > 1000 THEN GOTO 1146
8030  IF GAIN = 0 THEN GOTO 1146
8040  IF GAIN > 2.1 THEN GOTO 1146
8050  GOTO 1149
```

We claim:

1. Apparatus for causing the coordinated motion of a paralyzed human limb comprising:
   a microprocessor responsive to a feedback signal for generating a command signal indicating a desired effort by the muscles controlling said coordinated motion of said limb,
   at least three transcutaneous electrodes for placement in a spaced apart pattern on the skin above said muscles,
   a stimulator responsive to said command signal for generating a pair of stimulation signals comprising alternately generated pulses of stimulation energy,
   means for applying said stimulation signals across pairs of said electrodes, and
   feedback means responsive to the motion of said limb for generating said feedback signal.

2. Apparatus according to claim 1 wherein said stimulator comprises:
   pulse generating means for generating a low voltage pulsed signal corresponding to said command signal, and
   means electrically isolated from said pulse generating means for generating said pair of stimulation signals at high voltages.

3. Apparatus for controlling a paralyzed human muscle comprising:
   control means for generating a command signal representing a desired effort from said muscle,
   signal processing means responsive to said command signal for generating a series of pulsed stimulation signals,
   electrode means for applying said stimulation signals to said muscle,
   dynamic load means for yieldingly resisting movement of said muscle and
   sensing means for generating a feedback signal representing the response of said muscle to the combined effects of said stimulation signals and said dynamic load;
   said control means including means for reading said feedback signal, comparing the response of said muscle to a desired response and modifying said command signal in accordance with the comparison which is so made.

4. Apparatus for controlling a human muscle comprising:
   digital processing means for generating a digital command,
   digital to analog converting means for converting said digital command into an analog command signal,
   signal processing means responsive to said analog command signal for generating a pair of stimulation signals comprising alternately generated pulses; said pulses having an amplitude corresponding to the amplitude of said analog command signal,
   electrode means for applying said stimulation signals to said muscle,
   dynamic load means for yieldingly resisting movement of said muscle;
   sensing means for generating an analog feedback signal representing the response of said muscle to the combined effects of said stimulation signals and said dynamic load, and analog to digital converting means for converting said analog feedback signal into a digital feedback signal; said digital processing means including means for reading said digital feedback signal, comparing the response of said muscle to a desired response and modifying said digital command in accordance with the comparison which is so made.

5. Apparatus according to claim 4 wherein said stimulation signals are each pulsed at a frequency between about 55 and 65 Hz, said pulses having a duration of approximately 500 microseconds.

6. Apparatus according to claim 5 wherein said electrode means comprises three electrodes connected in pairs for reception of said stimulation signals.

7. Apparatus according to claim 6 wherein one of said electrodes serves as a common ground, one of said stimulation signals being applied across said common electrode and a second of said electrodes and the other of said stimulation signals being applied across said common electrode and the third of said electrodes.

8. Apparatus according to claim 7 and further comprising means for adhering said electrodes to an area of skin which covers said muscle.

9. Apparatus according to claim 5 wherein said pulses have an amplitude between about 0 and 255 volts when measured across their respective electrode pairs at said skin area.

10. Apparatus according to any of claims 4–9 and further comprising profile generating means for generating a reference signal having a profile representing said desired response and means for applying said reference signal to said analog to digital converting means.

11. Apparatus according to any claim 9 wherein said signal processing means comprises pulse generating means for generating a pair of alternatingly pulsed synchronizing signals, amplifying means for amplifying said synchronizing signals in correspondence with said analog command signal, and transformer means responsive to said amplified synchronizing signals for generating said stimulation signals.

12. Method of causing coordinated movement of a paralyzed human limb comprising the steps of applying at least three transcutaneous stimulation electrodes at spaced positions on the skin above a muscle controlling said limb, applying voltage pulses in an alternating sequence across different electrode pairs, generating a sensing signal corresponding to the movement of said limb, and adjusting the amplitude of said voltage pulses in response to said sensing signal.

13. Method of causing a predetermined movement of a paralyzed limb of a human being comprising the steps of:
  (1) mounting at least three electrodes for stimulating different portions of a movement muscle for said limb,
  (2) causing contraction of said muscle by applying pulses of stimulating energy alternately across different pairs of said electrodes,
  (3) applying a dynamic force against said limb to partially counteract the effort of said muscle,
  (4) generating a feedback signal representing movement achieved by said limb,
  (5) adjusting the amplitude of said pulses in response to said feedback signal, and
  (6) terminating the application of said pulses when said predetermined movement has been achieved.

14. Method according to claim 13 wherein said electrodes are applied in spaced apart positions upon the skin of said human being immediately above said muscle.

15. Method according to claim 14 wherein the amplitude of said pulses is maintained at a level below about 255 volts.

16. Method according to any of claims 13–14 wherein the pulses applied to each electrode pair have a duration of about 500 microseconds and a frequency ranging between about 55 and 65 Hz.

17. Method according to claim 16 wherein said frequency is 60 Hz.

* * * * *

UNITED STATES PATENT AND TRADEMARK OFFICE
CERTIFICATE OF CORRECTION

PATENT NO. : 4,492,233

DATED : January 8, 1985

INVENTOR(S) : Petrofsky et al.

It is certified that error appears in the above-identified patent and that said Letters Patent is hereby corrected as shown below:

Column 3, line 47, --plate-- should be inserted after "clamp".

Column 4, line 45, "hypoallerqenic" should be --hypoallergenic--.

Column 6, line 65, "inut" should be --input--.

Column 15, line 37, (claim 11) delete "any".

Column 16, line 21, (claim 13), insert --predetermined-- before "dynamic".

Page 2, column 2, lines 1 and 2, --the Isometric Cat Soleus Muscle, Rack and Westbury, J. Physiol. (1969), 204, pp. 443-460.-- should be inserted following line 23 after "The Effects of Length and Stimulus Rate on Tension in".

Signed and Sealed this

Twenty-fifth Day of June 1985

[SEAL]

Attest:

DONALD J. QUIGG

Attesting Officer        Acting Commissioner of Patents and Trademarks